(12) United States Patent
Dvorak et al.

(10) Patent No.: US 9,005,918 B2
(45) Date of Patent: Apr. 14, 2015

(54) ALGAE BIOREACTOR, SYSTEM AND PROCESS

(75) Inventors: Stephen W. Dvorak, Chilton, WI (US); Douglas Van Ornum, Chilton, WI (US)

(73) Assignee: DVO, Inc., Chilton, WI (US)

(*) Notice: Subject to any disclaimer, the term of this patent is extended or adjusted under 35 U.S.C. 154(b) by 0 days.

(21) Appl. No.: 13/995,240

(22) PCT Filed: Dec. 15, 2011

(86) PCT No.: PCT/US2011/065143
§ 371 (c)(1),
(2), (4) Date: Jun. 18, 2013

(87) PCT Pub. No.: WO2012/087741
PCT Pub. Date: Jun. 28, 2012

(65) Prior Publication Data
US 2013/0280757 A1    Oct. 24, 2013

Related U.S. Application Data

(60) Provisional application No. 61/424,959, filed on Dec. 20, 2010.

(51) Int. Cl.
*C12P 1/00*      (2006.01)
*C12N 1/12*      (2006.01)
*C12M 1/00*      (2006.01)

(52) U.S. Cl.
CPC ............... *C12M 21/02* (2013.01); *C12M 27/20* (2013.01); *C12M 29/06* (2013.01); *C12M 31/08* (2013.01)

(58) Field of Classification Search
USPC ..................................... 435/41, 257.1, 283.1
See application file for complete search history.

(56) References Cited

U.S. PATENT DOCUMENTS

| | | | |
|---|---|---|---|
| 4,073,089 | A | 2/1978 | Maginnes et al. |
| 4,541,752 | A | 9/1985 | Phillips |
| 5,573,669 | A | 11/1996 | Jensen |
| 6,237,284 | B1 | 5/2001 | Erickson |
| 6,254,775 | B1 | 7/2001 | McElvaney |
| 6,451,589 | B1 | 9/2002 | Dvorak |
| 6,602,703 | B2 | 8/2003 | Dutil |
| 6,613,562 | B2 | 9/2003 | Dvorak |
| 6,780,321 | B2 | 8/2004 | Chanrai et al. |
| 7,078,229 | B2 | 7/2006 | Dvorak |
| 7,179,642 | B2 | 2/2007 | Dvorak |
| 8,202,721 | B2 | 6/2012 | Dvorak |
| 2005/0064577 | A1 | 3/2005 | Berzin |
| 2005/0239182 | A1 | 10/2005 | Berzin |
| 2005/0260553 | A1 | 11/2005 | Berzin |
| 2007/0114173 | A1 | 5/2007 | Dvorak |
| 2007/0289206 | A1 | 12/2007 | Kertz |
| 2008/0009055 | A1 | 1/2008 | Lewnard |
| 2008/0050800 | A1 | 2/2008 | McKeeman et al. |
| 2008/0087165 | A1 | 4/2008 | Wright et al. |
| 2008/0178739 | A1 | 7/2008 | Lewnard et al. |
| 2008/0268302 | A1 | 10/2008 | McCall |
| 2009/0011492 | A1 | 1/2009 | Berzin |
| 2009/0130706 | A1 | 5/2009 | Berzin et al. |
| 2009/0170184 | A1 | 7/2009 | Shepherd et al. |
| 2009/0211150 | A1 | 8/2009 | Wu et al. |
| 2009/0275120 | A1* | 11/2009 | Koch et al. .................. 435/292.1 |

FOREIGN PATENT DOCUMENTS

| | | |
|---|---|---|
| EP | 0978232 A2 | 2/2000 |
| WO | 95/32611 A1 | 12/1995 |
| WO | 2009/002772 A2 | 12/2008 |
| WO | 2009/149519 A1 | 12/2009 |

OTHER PUBLICATIONS

Brainard, L.; Algae May Help Fuel the Future; A Preston Man is Helping; Republican Leader; http://ww.bluffcoutryreader.com; Jan. 14, 2009; 5 pages.

Chisti, Y.; Biodiesel from Microalgae Beats Bioethanol; School of Engineering—Massey University; Trends in Biotechnology vol. 26 No. 3; Jan. 24, 2008; 6 pages.

Javanmardian, M. et al., Design and Operation of an Algal Photobioreactor System; The University of Michigan Ann Arbor; Adv. Space Res. vol. 12, No. 5; Copyright © 1991 COSPAR; 5 pages.

Lee, C. et al.; High-Density Algal Photobioreactors Using Light-Emitting Diodes; University of Michigan Ann Arbor; Biotechnology and Bioengineering; vol. 44, pp. 1161-1167; Copyright © 1994 John Wiley & Sons, Inc.

Niranajne, M.; Seminar on Algae as Bio Reactor; Chemical Engineering Department—S.V. National Institute of Technology; 60 pages, 2009.

Notification of International Search Report and Written Opinion; International Application No. PCT/US2011/1065143; Apr. 6, 2012; 8 pages.

Ogbonna, J. et al., Industrial-Size Photobioreactors; CHEMTECH, 27(7), pp. 43-49; Copyright © 1997 by the American Chemical Society.

(Continued)

*Primary Examiner* — Karen Cochrane Carlson
*Assistant Examiner* — Natalie Moss
(74) *Attorney, Agent, or Firm* — Whyte Hirschboeck Dudek S C (57) ABSTRACT

The present disclosure provides an algae bioreactor and process. The algae bioreactor includes a container with an inlet and an outlet. An algae suspension present in the container interior moves from an inlet to an outlet along a flowpath. A light assembly, a liftwall, and a gas conduit are located in the container interior. The gas conduit extends along a length of the container and emits gas bubbles into the algae suspension. A diffuser is located on a bottom wall of the container, The flowpath, the liftwall, the gas conduit, and the diffuser produce an active flow of the algae from the container inlet to the container outlet. The container may be a deep-vessel container.

20 Claims, 5 Drawing Sheets

(56) References Cited

OTHER PUBLICATIONS

Putt, R.; Algae as a Biodiesel Feedstock; A Feasibility Assessment; Department of Chemical Engineering—Auburn University, Alabama; Apr. 7, 2008; 47 pages.

Stepan, D., et al.; Carbon Dioxide Sequestering Using Microalgal Systems; Energy & Environmental Research Center—University of North Dakota; Feb. 2002; 32 pages.

Tucker, L.; Taking the High Road Leads Oregon Inventor to Minnesota; Daily Journal of Commerce (Portland, OR); http://findarticles.com; Mar. 31, 2008; printed Jul. 10, 2009; 2 pages.

Woertz, I.; Lipid Productivity of Algae Grown on Dairy Wastewater as a Posible Feedstock for Biodiesel; Califoria Polytechnic University, San Luis Obispo; Dec. 2007; 87 pages.

* cited by examiner

ALGAE BIOREACTOR, SYSTEM AND PROCESS

CROSS REFERENCE TO RELATED APPLICATION

This application claims the benefit of U.S. Provisional Application No. 61/424,959 filed on Dec. 20, 2010, the entire content of which is incorporated by reference herein.

BACKGROUND

Social and political debate continues to escalate for two, (albeit somewhat related) issues: (1) consumption of finite fossil fuel, and (2) the growing concentration of carbon dioxide in the global atmosphere. Some estimates indicate that 97% of the fuel used in U.S. transportation is petroleum-based, with 66% of U.S. oil imported from foreign sources. The world's voracious appetite for petroleum-based fuel along with the consumption of other fossil fuels (such as coal) has led to the recognition of carbon dioxide as the largest atmospheric pollutant. Despite controversy over the true environmental impact caused by increased concentrations of atmospheric carbon dioxide, efforts are underway to raise social awareness to these issues and find solutions to the same.

Amid this social landscape, the interest in sustainable, alternate fuel sources continues to grow. The ability of algae to address the issues of (1) an alternative fuel source and (2) increased concentrations of atmospheric carbon dioxide issues is known. Algae have received much attention for the ability to not only remove carbon dioxide from the atmosphere but also the ability to produce fuel and biomass from the carbon dioxide. Algae are fast growing with a high lipid content. Algae farms are systems that use algae to convert carbon dioxide into a natural oil—a viable alternative energy source to petroleum-based fuels. In addition to energy, algae have many other applications including pharmaceuticals, cosmetics, and a food source.

However, many obstacles face large-scale implementation of algae farms. Open algae farms, for example, face substantial limitations. Limitations to open algae farms include poor light utilization, evaporative losses, diffusion of $CO_2$ into the atmosphere, the requirement for large areas of land, exposure to weather unpredictability, contamination, and poor temperature control. Open algae farms are also are not viable in colder climates—which imposes a significant geographic limitation.

A need exists for devices, systems and processes that produce algae. A need also exists for a closed algae production system that reduces the amount of carbon dioxide present in the atmosphere. A further need exists for algae production devices, processes and systems adaptable for use in any climate zone.

SUMMARY

The present disclosure is directed to an algae bioreactor, system and process. The present algae bioreactor utilizes a unique active flow to cultivate and produce algae. The algae bioreactor may be a stand-alone device or one component of a larger energy production system. The present algae bioreactor may be a closed container or an open system. The present algae bioreactor may be a deep vessel algae bioreactor. An advantage of the present algae bioreactor is that it has no geographical limitation—it is equally adaptable in warm climates as well as cold climates.

In an embodiment, an algae bioreactor is provided and includes a container with an inlet and an outlet. An algae suspension is present in the container. A flowpath moves from the inlet to the outlet. A light assembly and a liftwall are located in the container interior. A gas conduit extends along a length of the container interior, the gas conduit emitting gas bubbles into the algae suspension. The flowpath and the emitted gas bubbles move the algae in a helical motion around the liftwall. In an embodiment, the emitted gas bubbles are carbon dioxide bubbles.

In an embodiment, a diffuser is located below the light assembly and/or the liftwall. The diffuser emits gas bubbles. The flowpath, the emitted gas bubbles from the gas conduit and the diffuser produce an active flow of the algae from the inlet to the outlet.

In an embodiment, the container is a deep-vessel container.

The present disclosure provides another algae bioreactor. In an embodiment, an algae bioreactor is provided and includes a container with an inlet and an outlet. An algae suspension is present in the container interior. A flowpath moves from the inlet to the outlet. In the container interior are a light assembly and a liftwall. A gas conduit extends along a length of the container interior. The gas conduit emits gas bubbles into the algae suspension. A diffuser is located on a bottom wall of the container. The diffuser emits gas bubbles into the algae suspension. The flowpath, the liftwall, the gas conduit, and the diffuser produce an active flow of the algae from the container inlet to the container outlet.

In an embodiment, the outlet is in fluid communication with a harvest tank.

In an embodiment, the container is a deep-vessel container.

The present disclosure provides a process. In an embodiment, a process is provided and includes introducing an algae suspension into a container. The container has an inlet, an outlet, a light assembly, a liftwall, a gas conduit, and a diffuser. The process includes actively flowing the algae suspension from the container inlet to the container outlet under photosynthesis conditions.

In an embodiment, the process includes helically moving the algae around the liftwall.

In an embodiment, the process includes growing the algae to a harvest density and harvesting the algae at the harvest density from the outlet. The algae may be continuously or intermittently harvested from the outlet.

In an embodiment, the process includes actively flowing the algae suspension through a deep-vessel container.

An advantage of the present disclosure is an improved algae bioreactor.

An advantage of the present disclosure is an algae bioreactor with an improved flow profile.

An advantage of the present disclosure is an improved flow system suitable for an open algae farm or a closed algae bioreactor.

An advantage of the present disclosure is a sustainable closed algae production system.

An advantage of the present disclosure is a closed, deep-vessel algae production system.

An advantage of the present disclosure is a closed algae bioreactor and production system that is scalable to meet large-scale fuel consumption needs of businesses, municipalities, states, and countries.

An advantage of the present disclosure is a system and process for reducing the amount of carbon dioxide in the atmosphere while simultaneously producing a sustainable biofuel.

An advantage of the present disclosure is the production of an algae-based energy source.

An advantage of the present disclosure is a process for removing nitrogen and/or phosphorus from wastewater.

DETAILED DESCRIPTION

The disclosure provides a bioreactor. A "bioreactor" is a device or a system that supports a biologically active environment. In an embodiment, the bioreactor is an algae bioreactor. An "algae bioreactor or "ABR" as used herein, is a structure that supports the growth of a photosynthesizing organism such as algae, for example. Algae cultivation requires water, carbon dioxide, light, and minerals. The end product of algae cultivation is a biomass with myriad applications (food, fertilizer, bioplastics, dyes and colorants, chemical feedstock, pharmaceuticals, pigments, chemical intermediates, biofuel, fuel, clean energy, pollution control).

Figure 1:
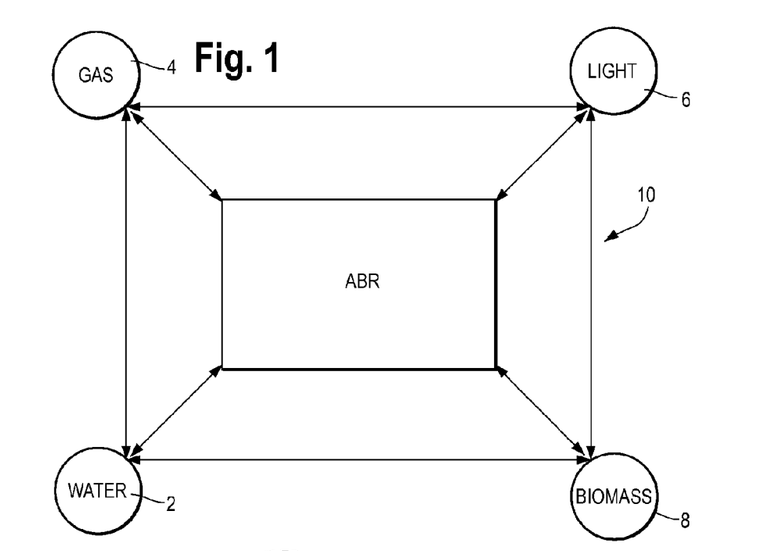
FIG. 1 is a schematic representation of the interrelationship between an algae bioreactor, and the inputs/outputs therefrom in accordance with an embodiment of the present disclosure.

FIG. 1 is a schematic diagram showing the interrelationships between, the inputs for algae growth—water 2, gas 4, light 6, the present ABR, and the output, biomass. The water 2 may be freshwater or seawater. The freshwater may be surface water (lakes, rivers), or groundwater. The water source may be effluent water from a manufacturing process, a power plant, an anaerobic digester, a wastewater treatment plant, and any combination thereof.

The gas 4 is carbon dioxide alone or in combination with one or more other gases such as nitrogen, hydrogen, nitrogen dioxide, helium, and/or sulfur dioxide. Nonlimiting examples of suitable gas sources for the present ABR include the atmosphere, vehicles, power plants, manufacturing plants (cement, automobile, brewery, fertilizer, steel), digesters, any combustion engine, and any combination of the foregoing.

The light 6 is natural light (sunlight), artificial light (electric light), and combinations thereof. Algae need only about $\frac{1}{10}^{th}$ the amount of light received from sunlight. Direct sunlight is often too strong for many types of algae.

The biomass 8 is the product produced from the present algae bioreactor. As discussed in detail below, the present algae bioreactor converts light, gas, and water into the biomass 8. The biomass 8 has many applications. An advantage of the present algae bioreactor is the sustainability between the inputs, the ABR, and the output. For example, the water input into the ABR can be recycled and reused. The biomass produced from the ABR may be converted into biofuel that may be combusted to produce the gas and/or the heat for the ABR. The energy from the biomass may be used to power artificial light for the ABR. Alternatively, the biomass may be burned to produce the gas and/or the heat for the ABR.

Figure 2:
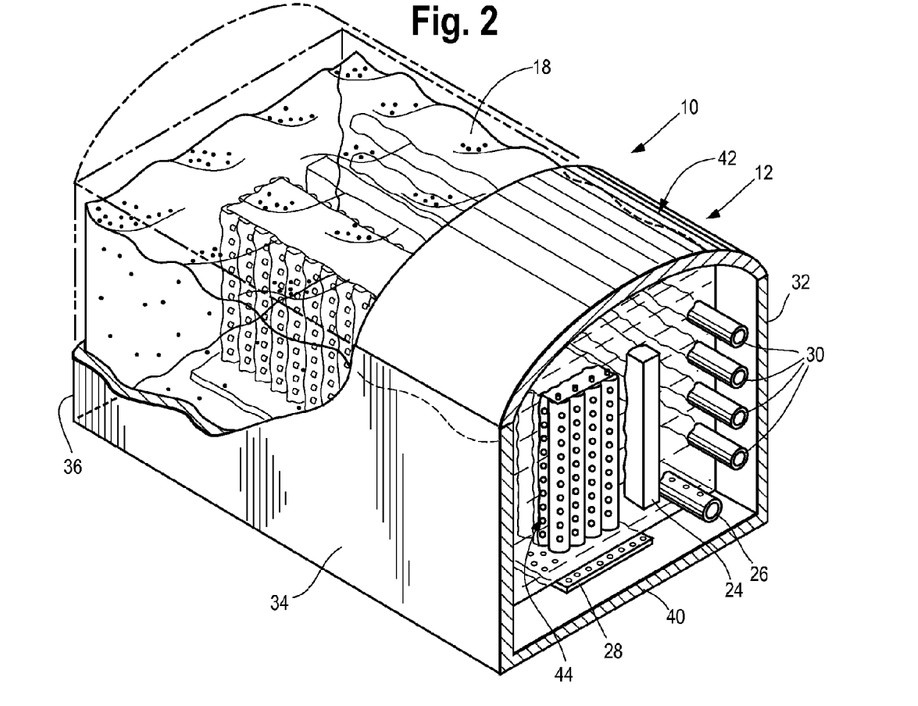
FIG. 2 is a cutaway perspective view of an algae bioreactor in accordance with an embodiment of the present disclosure.
Figure 3:
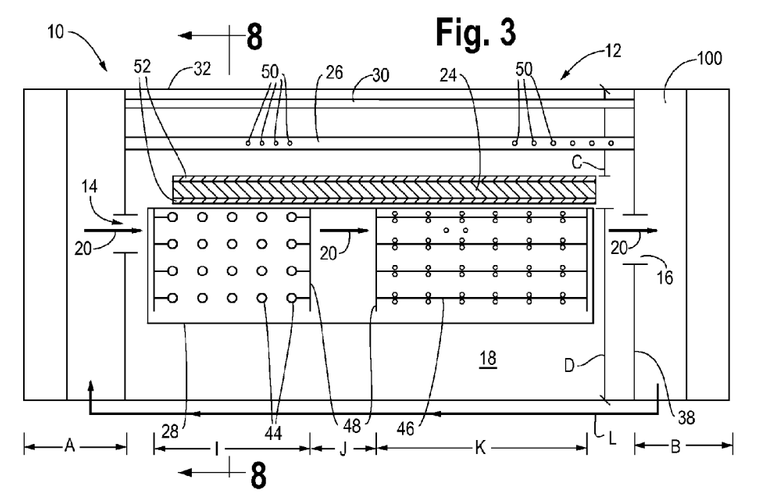
FIG. 3 is plan view of an algae bioreactor in accordance with an embodiment of the present disclosure.

In an embodiment, an algae bioreactor (ABR) 10 is provided as shown in FIGS. 2 and 3. The algae bioreactor 10 includes a container 12 having an inlet 14 and an outlet 16. The container 12 holds an algae suspension 18. A flowpath 20 moves the algae suspension 18 from the inlet 14 to the outlet 16. The algae bioreactor 10 also includes an inlet portion A and an outlet portion B. The inlet portion A includes fluid communication to a water source, optional water pre-treatment systems (filtration), and pumping systems. The outlet portion B includes a harvest portion. In an embodiment, the algae suspension is recirculated from outlet portion B back to inlet portion A.

Located in the interior of the container 12 are a light assembly 22 a liftwall 24, and a gas conduit 26. The algae bioreactor 10 may optionally include a diffuser 28, and/or a thermal assembly 30. Although disclosed in the singular, it is understood that the algae bioreactor 10 may include one or more of any of the foregoing components.

1. Container

The container 12 has opposing first and second sidewalls 32, 34 an inlet wall 36 and an outlet wall 38 as shown in FIGS. 2 and 3. The container 12 also has a bottom wall 40 and an optional top wall 42. The top wall 42 may be removable and the algae bioreactor 10 is operable with or without the topwall 42. The container walls define an interior. The container 12, and/or the walls thereof, may be transparent, translucent, or opaque. The container walls may be made of glass, polymeric material, metal, concrete, insulative material, and any combination thereof. The walls of the bioreactor may be flexible or rigid.

Figure 3A:
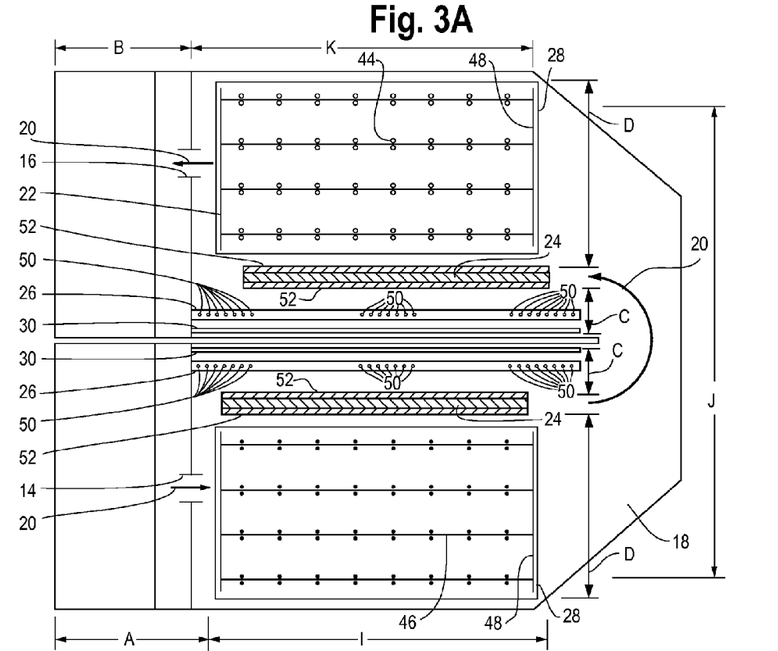
FIG. 3A is a plan view of an algae bioreactor in accordance with an embodiment of the present disclosure.

The container 12 is water-tight. One, some, or all of the container inner surfaces may include a reflective material, a light source, a thermal element, and any combination thereof. The container 12 may have any desired shape. In an embodiment, the container has a rectangular shape as shown in FIG. 3. In another embodiment, the container has a u-shape as shown in FIG. 3A.

The container may be an open container (open system) or a closed container (closed system). The open container does not include top wall 42. In an embodiment, the container is a closed container and includes the top wall 42. The top wall 42 may be made of glass, polymeric material, metal, concrete, and any combination thereof. The top wall 42 may be transparent, translucent, or opaque. In an embodiment, the top wall 42 is transparent and/or translucent thereby permitting sunlight to enter the container interior. A closed container advantageously provides greater control of environmental conditions within the container and minimizes contamination. A closed container also prevents the evaporation of water.

The container 12 can be located in a body of water (ocean, lake or shore line thereof), on the ground, or in the ground. In an embodiment, the container 12 is located or otherwise buried in the ground. Greater than 50%, or from about 50% to about 99% of the container exterior surface area may be in contact with the ground. The top wall 42 may be exposed to sunlight. Bounded by no particular theory, it is believed that the buried (or partially buried) container is insulated by the surrounding ground which maintains the container interior at a temperature no less than 10-12° C. (50-54° F.) to about 38° C. (100° F.). This is particularly advantageous when the algae bioreactor 10 is located in colder climates and/or colder geographical regions with significant seasonal temperature change. The container 12 may also be located in a body of water such as on the shore of a freshwater lake or on the shore of an ocean or a sea.

An advantage of the present bioreactor is that the size of the container 12 is scalable. The length, width, and/or depth of the container 12 may be varied for small-scale biomass production or large-scale biomass production. Thus, the container 12 may be configured to contain an algae suspension volume from 10 liters, or 100 liters, or 1,000 liters, or 10,000 liters to an upper algae suspension volume of 1,000, or 10,000, or 100,000, or 1,000,000 times these volumes. In some embodiments, the container 12 has an upper volume of 1,000,000 liters, or 10,000,000 liters, or 100,000,000 liters or more.

In another embodiment, the container 12 has an inner width from about 9 m to about 15 m, an inner length from about 4 m to about 20 m, and an inner depth from about 1 m, or about 2 m, or about 3 m to about 20 m. It is understood that the thickness of the container walls (and thereby the outer dimensions of the container) may vary upon up-scale. In a further embodiment, the container 12 is 20 feet long (6 m), 20 feet wide (6 m), and has a depth of 16 feet (5 m).

The inlet 14 is in fluid communication with a water source and a pump (device or system) (not shown). The outlet 16 may be in fluid communication with a harvest tank 100. Water (and optionally other materials) is introduced into the container 12 by way of the inlet 14. The pump moves the algae suspension 18 along the flowpath 20 to the outlet 16. The container 12 may also include one or more nutrient ports for introducing nutrients into the algae suspension 18.

In an embodiment, the algae bioreactor 10 includes one or more pumps in operative communication with the inlet. The pumps move the algae suspension along the flowpath 20 at a flow rate from 0 liters/day, or greater than 0 liters/day, or 1 liter/day to 40,000 liters/day.

In an embodiment, the container 12 is a deep-vessel container. The term "deep-vessel container," as used herein, is a container having a depth that cannot support photosynthesis from natural light (sunlight). In other words, water present in the deep-vessel container has a depth that cannot support photosynthesis by way of sunlight. Sunlight supported algal photosynthesis has a maximum depth of about 1.5 feet. In an embodiment, the deep vessel container has depth greater than 1.5 feet, or from greater than 1.5 feet, or 2 feet, or 3 feet to about 20 feet, or about 30 feet, or about 40 feet, or about 50 feet, or about 60 feet, or about 100 feet. In a further embodiment, the container 12 is a closed deep-water container and has a depth from about 15 feet to about 25 feet, or about 20 feet.

The deep-vessel container is distinct compared to conventional algae raceway ponds. Conventional raceway ponds are typically lined with plastic or cement, are about 20 to 35 cm deep to ensure adequate exposure to sunlight. Paddlewheels provide motive force and keep the algae suspended in the water. The ponds are supplied with water and nutrients, and mature algae are continuously removed at one end. The deep-vessel container holds water at a depth greater than 1.5 feet (0.5 m)—a water depth that cannot sustain photosynthesis from sunlight.

2. Algae Suspension

The container 12 holds an organism. An "organism," as used herein, is an individual form of life. An organism can be a prokaryotic organism or an eukaryotic organism. The organism can be an autotrophic organism or a heterotrophic organism. Nonlimiting examples of organisms include plants, animals, bacterium, protist, and/or fungus.

In an embodiment, the container 12 holds or otherwise contains a photosynthesizing microorganism medium. As used herein, the term "photosynthesizing microorganism" is an organism that is capable of utilizing light as an energy source to convert carbon dioxide into organic compounds. In an embodiment, the photosynthesizing microorganism medium is the algae suspension 18. The term "algae suspension," as used herein, is a solid-in-liquid suspension composed of a plurality of algae organisms or algae cells (solid phase) dispersed in water (aqueous or liquid phase). The algae suspension 18 may include other solid components (i.e., algae nutrients such as nitrogen-, phosphorus-, and/or sulfur-based compounds) and/or a gas component.

The algae suspension 18 includes algae as a solid phase. The term "algae," as used herein, is any autotrophic organism capable of photosynthesis that lives in water (either freshwater and/or seawater). The term "algae" includes "macroalgae" (seaweed) and "microalgae" (small algae). The term "algae" includes diatoms (Bacillariophyceae), green algae (Chlorophyceae), blue-green algae (Cyanophyceae), golden algae (Chrysophyceae or chrysophyte), brown algae, and/or red algae. The algae can be any algae species including macro algae, micro algae, marine algae, or freshwater algae. Nonlimiting examples of suitable algae include chiarella vulgaris, haematococcus, stichochoccus, bacillariophyta (golden algae), cyanophyceae (blue green algae), chlorophytes (green algae), *chlorella*, botryococcus braunii, cyanobacteria, prymnesiophytes, coccolithophorads, neochloris oleoabundans, scenedesmus dimorphus, atelopus dimorphus, euglena gracilis, dunalielia, dunaliella salina, dunaliella tertiolecta, diatoms, bacillariophyta, chlorophyceae, phaeodactylum tricornutunum, stigmatophytes, dictyochophytes, and pelagophytes. The algae may be single cells, colonies, clumps, and any combination thereof. The algae can be natural algae, or can be genetically-modified algae.

The algae suspension 18 may contain a monoculture (single algae species) or a multiculture (multiple algae species). In an embodiment, the algae suspension contains a monoculture.

Algae is an efficient biological factory capable of taking a waste form of carbon (such as $CO_2$) and converting it into a high density liquid form of energy (natural oil). Algae are composed of carbohydrates, protein, and natural oils. Algae can produce up to 60% (or more) of their body weight in the form of natural oil, such as triacylglycerols.

The chemical compositions for several nonlimiting examples of algae are provided in Table 1 below.

TABLE 1

Chemical Composition of Algae Expressed on a Dry Matter Basis (%)

| Strain | Protein | Carbohydrates | Lipis | Nucleic acid |
|---|---|---|---|---|
| Seenedesmus obliquus | 50-56 | 10-17 | 12-14 | 3-6 |
| Seenedesmus quadricauda | 47 | — | 1.9 | — |
| Seenedesmus dimorphus | 8-18 | 21-52 | 16-40 | — |
| Chlamydomonas rheinhardii | 48 | 17 | 21 | — |
| Chlorella vulgaris | 51-58 | 12-17 | 14-22 | 4-5 |
| Chlorella pyrenoidosa | 57 | 26 | 2 | — |
| Spirogyra sp. | 6-20 | 33-64 | 11-21 | — |
| Danaliella bioculata | 49 | 4 | 8 | — |
| Dunaliella salina | 57 | 32 | 6 | — |
| Euglena gracilis | 39-61 | 14-18 | 144-20 | — |
| Prymnesium parvum | 28-45 | 25-33 | 22-38 | 1-2 |
| Tetraselmis maculata | 52 | 15 | 3 | — |
| Porphyridium cruentum | 28-39 | 40-57 | 9-14 | — |
| Spirulina platensis | 46-63 | 8-14 | 4-9 | 2-5 |
| Spirulina maxima | 60-71 | 13-16 | 6-7 | 3-4.5 |
| Synechoccus sp. | 63 | 15 | 11 | 5 |
| Anabaena cylindrica | 43-56 | 25-30 | 4-7 | — |

Algae contain one or more light absorbing pigments. For example, all plant, algae and cyanobacteria contain chlorophyll A, cyanobacteria contain phycobilm, green algae contain chlorophyll B, red algae contain phycoerythm, brown algae and diatoms contain fucoxanthm. These light absorbing pigments drive photosynthesis in the algae.

The algae suspension 18 also includes a liquid phase. The liquid phase may be fresh water or salt water. The liquid phase may include dissolved solids such as minerals and nutrients. The liquid phase may also include effluent from an anaerobic digester, effluent from a water treatment plant, and/or effluent water from a manufacturing/power plant, etc. The container 12, the algae suspension 18, the light assembly 22, and the gas conduit 26 provide an environment for photosynthesis conditions. As used herein, "photosynthesis conditions" are water, temperature, nutrient ($CO_2$), illumination (light), and pH parameters within the bioreactor suitable to promote the growth of a photosynthesizing organism (such as algae) to a desired mass, a desired density, and/or to a desired lipid content.

3. Light Assembly

The bioreactor 10 includes the light assembly 22. The light assembly 22 includes a light source and a support structure for the light source. The light assembly 22 includes one or more light sources that emit one or more wavelengths of light sufficient to support algae growth. The light source can be one or more light rods 44 and/or one or more light panels 46. The support structure 48 supports the light sources so that the light sources are suspended into the algae suspension 18. The light assembly 22 is moveable into and out of the container interior. The light assembly 22 is moveable into and out of the algae suspension 18.

The light assembly 22 may operate alone or in combination with natural light (i.e., solar light). The light source can be any type of artificial light. Nonlimiting examples of suitable artificial light for the light source include light emitting diode, organic light emitting diode, a gas discharge bulb, a laser, optical fiber, an incandescent bulb, a fluorescent bulb, a high pressure sodium bulb, a metal halide bulb, and any combination of the foregoing. In an embodiment, the light source is directly or indirectly powered by solar power. Direct solar power includes photovoltaic solar cells in operative communication with the light source. Indirect solar power includes photovoltaic solar cells that charge a power storage device (such as a battery), the power storage device subsequently powering the light source.

Figure 4:
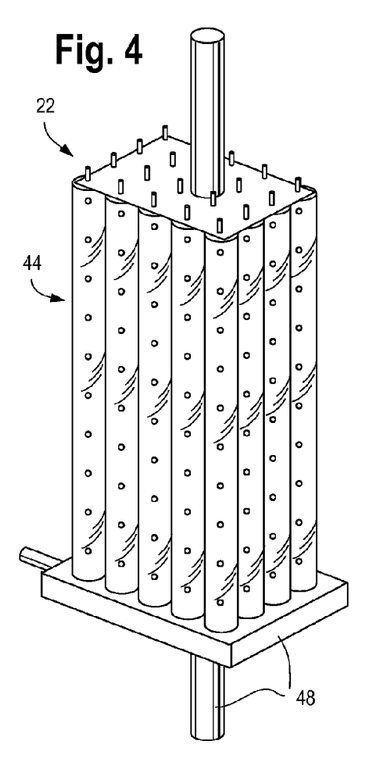
FIG. 4 is a perspective view of a light assembly in accordance with an embodiment of the present disclosure.

In an embodiment, the light assembly 22 includes an array of light rods 44 supported by support structure 48 as shown in FIG. 4. The light rods include a transparent waterproof tube made of a polymeric material or glass with a plurality of spaced-apart LEDs located along the length of the tube.

Figure 5:
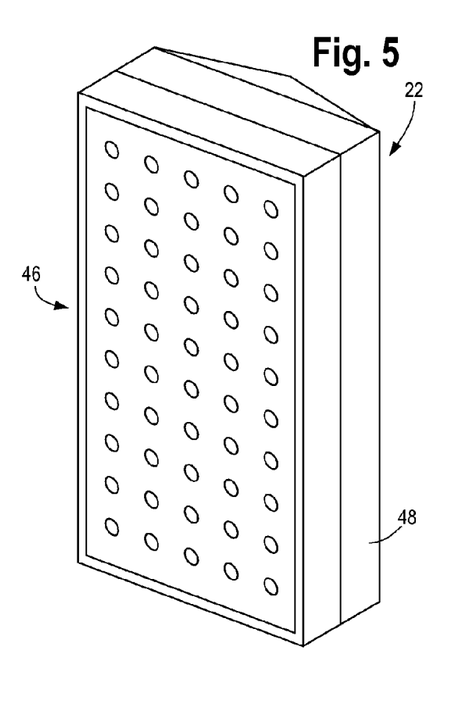
FIG. 5 is a perspective view of a light assembly in accordance with an embodiment of the present disclosure.

In an embodiment, the light assembly includes an array of light panels 46 supported by support structure 48 as shown in FIG. 5. The light panel includes a transparent waterproof pane made of a polymeric material or glass with a plurality of spaced-apart LEDs located therein. The light assembly 22 may include a combination of light rods 44 and light panels 46. It is understood that the light panel can be single pane or double pane.

The one or more light sources may be the same or different. The wavelength of each light source may be the same or different. The wavelength of each light source may be adjustable to maximize algae growth. The light assembly 22 and/or the container 12 may optionally include reflectors, light diffusers, lenses (lenticular, parabolic, Frensel, etc.) to disperse, amplify, direct, or otherwise intensify the light emitted from the individual light sources into the algae suspension 18.

The illumination of the light source may be continuous or intermittent (pulsed). Light intensity from the light source may be continuous or variable. For example, light intensity may be lower near the container inlet where algae density is lower whereas light intensity may be higher near the container outlet where algae density is higher.

Figure 6:
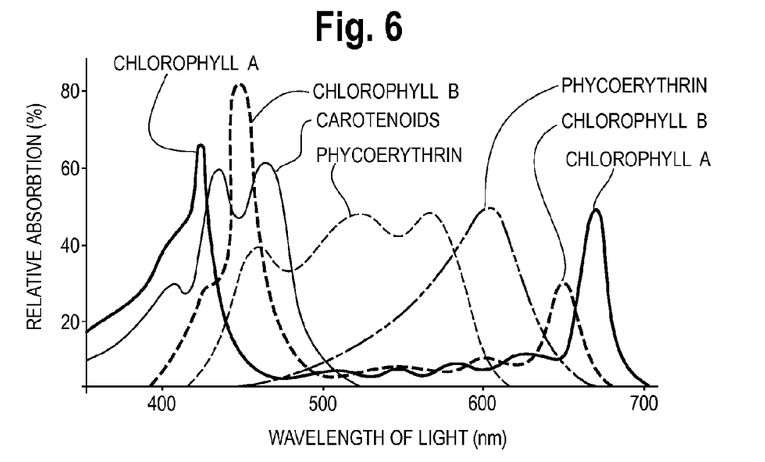
FIG. 6 is a graph showing light absorption spectra for various algae species.
Figure 7:
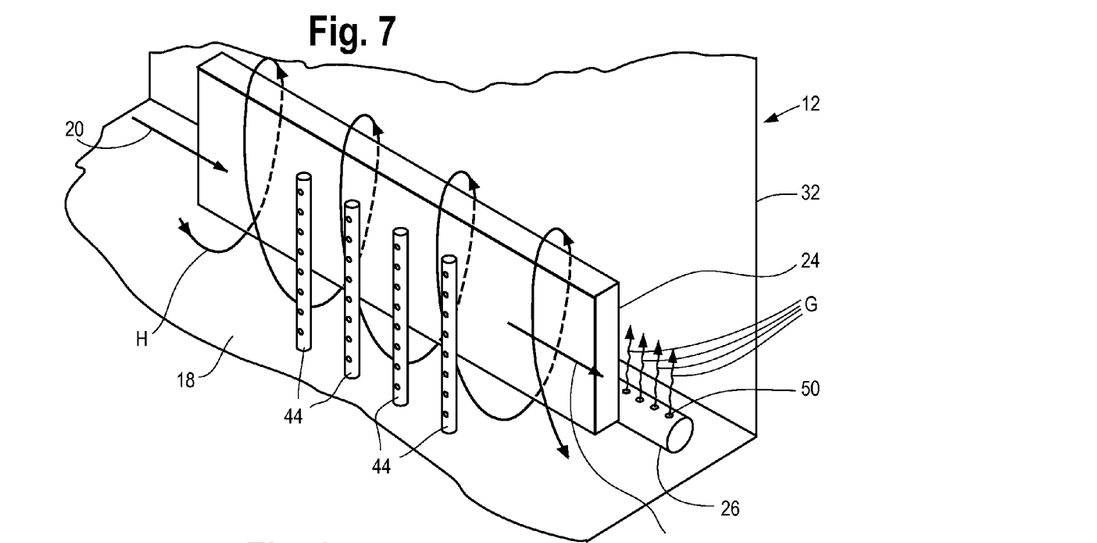
FIG. 7 is a schematic representation of a helical fluid flow in an algae bioreactor in accordance with an embodiment of the present disclosure

In an embodiment, the light source is selected to maximize algae growth. The algae and the light source are selected based on one or more light absorbing pigments belonging to the algae. In other words, the light source is mated with or matched to the algae so that the light emitted from the light source maximizes algae growth. The wavelength of the light source is matched to one or more peak absorption wavelengths of the algae. The graph in FIG. 6 shows nonlimiting examples of the absorption spectra for nonlimiting examples of algae. In an embodiment, the light source is selected so as to provide light with a wavelength from about 300 nm to about 800 nm.

In an embodiment, the algae are pre-conditioned and/or pre-adapted to the light wavelength and intensity expected to be experienced in the algae bioreactor.

The light assembly 22 is immersed (wholly or partially) in the algae suspension 18. The light assembly 22 is removable from the container interior. Similarly, each light source may also be removable from the container and/or removable from the light assembly 22.

The light intensity may be constant or may be variable. In an embodiment, the light intensity is lower in portions of the container where algae density is low (upstream, near the inlet) and light intensity is higher in portions of the container where the algae density is high (downstream, near the outlet). Algae density typically increases as the cultivation progresses.

The spacing between the light sources can vary. In an embodiment, the spacing between the light tubes can be from about 0.5 cm or about 1 cm to about 10 cm, or about 100 cm, or about 500 cm, or about 1000 cm or more. The space between individual light sources in the light assembly may be constant (static) or dynamic (variable).

In an embodiment, the light assembly 22 includes structure and mechanisms to move the individual light sources toward or away from each other. In a further embodiment, a sensor located among or between the light sources and immersed in the algae suspension detects light illumination and light intensity in the algae suspension, transmits this data to a processor/controller, the processor/controller directs a mechanism in operative communication with the individual light sources to move the light sources toward or away from each other. For example, the sensor may detect lower light intensity as the algae density increases. This data is communicated to the processor/controller which subsequently directs the mechanism to move the individual light sources of the light assembly closer to each other. The opposite is also possible with sensor detection of less dense algae concentration communicated to the processor/controller. The processor/controller subsequently directs the mechanism to move individual light sources away from each other.

In an embodiment, the light assembly 22 can occupy up to 5%, 10%, 20%, 40%, 50, or 60% of the total volume inside the algae bioreactor 10. Arrangement of the one or more light assemblies 22 can be adjusted based on a desired level and/or pattern of light distribution.

4. Liftwall

Figure 8:
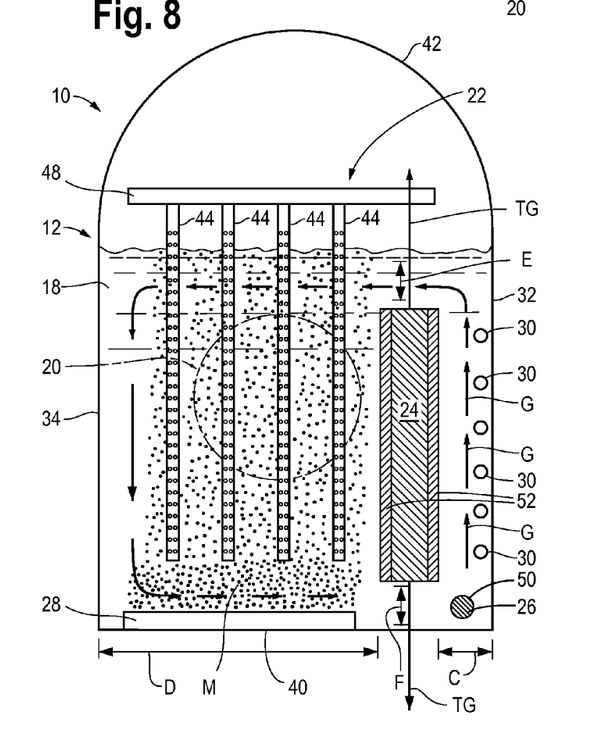
FIG. 8 is a sectional view taken along line 8-8 of FIG. 3.

Located in the interior of the container 12 is the liftwall 24. The liftwall 24 is wholly immersed in the algae suspension 18. The liftwall 24 is substantially parallel to, or parallel to, the flowpath 20. The liftwall 24 is substantially parallel to, or parallel to, sidewall 32 and/or sidewall 34. The liftwall 24 extends, wholly or partially, along the length of the container 12. The liftwall 24 separates, divides, or otherwise defines a portion C of the algae suspension and a portion D of the algae suspension as shown in FIGS. 3, 3A, and 8. The liftwall 24 is positioned above the container bottom wall 40 and below the algae suspension surface to provide flow points E and F (FIG. 8). Flow point E is between the top of the liftwall 24 and the surface of the algae suspension 18. Flow point F is between the bottom of the liftwall 24 and the bottom wall 40.

The algae bioreactor 10 includes one or more gas conduits 26. The gas conduit 26 extends along a length (whole length or partial length) of the container 12. The length of the gas conduit 26 itself may be continuous or intermittent. The gas conduit 26 may extend along any wall of the container.

In an embodiment, the gas conduit 26 is located in portion C of the container 12 and is parallel, or substantially parallel, to wall 32 and proximate to bottom wall 40. A plurality of spaced-apart jets 50 are located along the length of the gas conduit 26. The jets 50 emit a pressurized gas into the algae suspension 18. The gas may or may not be heated. The gas may or may not be cooled. The gas is $CO_2$ and may include optional other gases as disclosed above. Nonlimiting examples of optional other gases include nitrogen, oxygen, sulfur, helium, hydrogen, steam, air, an exhaust gas, and any combination thereof. An "exhaust gas," as used herein, is a gas resulting from the combustion of a hydrocarbon (such as methane gas), a biogas, and/or a fossil fuel (an oil, gasoline, coal). Nonlimiting examples of exhaust gas include carbon-based gas ($CO_2$), nitrogen-based gas ($NO_x$, where x=0, 1, 2), and sulfur-based gas ($SO_2$) and combinations thereof. The carbon dioxide provides nutrient to the algae.

In an embodiment, the gas is an exhaust gas of a combusted biogas (such as methane) produced from an anaerobic digester.

The pressurized gas forms gas bubbles in the algae suspension 18. The gas bubbles may be micro-bubbles, macro-bubbles, and combinations thereof. The term "micro-bubbles," as used herein, is a gas bubble within an aqueous medium such that the median bubble size (referred to herein as average bubble size or diameter) is from 1 micron to 100 microns. A "macro-bubble" is a gas bubble within an aqueous medium with a median bubble size greater than 100 microns.

Figure 9:
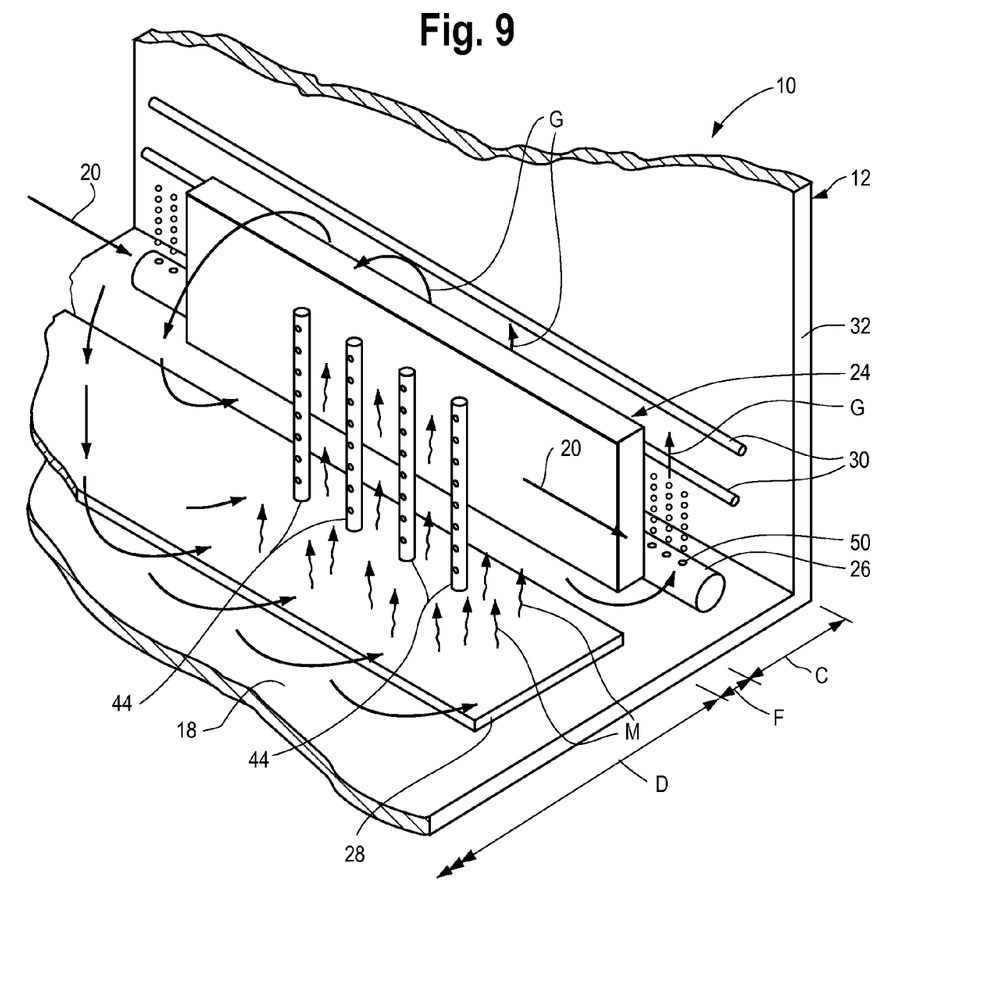
FIG. 9 is a breakaway perspective view of an algae bioreactor in accordance with an embodiment of the present disclosure.

The gas bubbles emitted by jets 50 produce a lift in portion C as shown by upward arrow G in FIGS. 8 and 9. The lift of G moves the algae upward and propels the algae (and/or the algae suspension) in portion C through flowpoint E and into portion D as shown in FIG. 8. Similarly, the lift from upward arrow G pulls algae from portion D through flowpoint F and into portion C. The upward lift of arrow G yields on overall rotational or rotary flow of the algae within the container interior. In other words, the lift G from the jets 50 propel or otherwise move or circulate the algae (and/or algae suspension) around the liftwall 24.

The flowpath 20 provides fluid flow along a first axis as shown in FIGS. 3, 3A, 7, and 9. The flowpath 20 is also shown in phantom in FIG. 8 (flowpath 20 coming out of the paper). The fluid flow along the flowpath 20 in combination with rotational flow from the lift G provided by the gas bubbles from jets 50 moves the algae cells in a helical motion around the liftwall 24. This helical movement of the algae flow is illustrated schematically by the serpentine arrow H in FIG. 7. The algae bioreactor 10 may include one or more gas conduits 26 in portion C and/or portion D to produce the lift G and the concomitant rotational or circular flow within the container 12.

In an embodiment, the liftwall 24 includes a light source as shown in FIGS. 3 and 8. A light panel 52 is located on one side, or both sides, of the liftwall 24. The light panel 52 emits light on algae helically flowing around the liftwall 24. In this way, the liftwall 24 simultaneously operates as a liftwall and a light source.

In an embodiment, the algae bioreactor includes a diffuser 28. One or more diffusers 28 extend along the bottom wall 40 of the container as shown in FIGS. 8 and 9. The diffuser 28 is located below the light assembly 22. The diffuser 28 emits macrobubbles and/or microbubbles of $CO_2$ and optional other gases. In an embodiment, the diffuser 28 emits microbubbles. The diffuser microbubbles advantageously provide (i) $CO_2$ in a form readily digestible by the algae, (ii) a scouring/cleansing effect to the light assembly by way of bubble impingement upon the light sources, and (iii) a mixing effect to the algae suspension. In this way, the diffuser microbubbles provide turbulent flow, or a micro-turbulent flow, within portion D of the container 12.

5. Active Flow

In an embodiment, the algae bioreactor 10 includes an active flow for the cultivation of algae. The term "active flow," as used herein, is a novel and unique flow profile created by (1) the flowpath 20, (2) the rotational flow within the container interior generated by the liftwall 24 and gas conduit 26 and the resultant lift G, and (3) the turbulent flow M (or micro-turbulent flow) from bubbles emitted by the diffuser 28. The active flow has a helical flow component (flowpath+liftwall+emitted bubbles from gas conduit and lift G) and (2) a turbulent flow component M (or a micro-turbulent flow component from the diffuser bubbles). The active flow moves or propels the algae around the liftwall 24 in a helical manner and simultaneously provides a turbulent flow (or micro-turbulent flow) of algae through the light assembly 22. The active flow simultaneously moves or flows the algae from the inlet 14 to the outlet 16. This is best seen in FIGS. 8 and 9. In FIG. 8, the flowpath 20 is shown by a phantom circle.

Applicants have discovered that the active flow unexpectedly improves algae cultivation—particularly for closed containers and/or deep-vessel containers. Bounded by no particular theory, the active flow is a unique flow profile that (1) brings the algae cells to the artificial light source(s), and (2) brings the nutrients ($CO_2$, minerals) to the algae cells. The present active flow (3) maximizes the number of photons that reach each algae cell, (4) distributes photons/light uniformly across the entire algae suspension, (5) maintains the algae homogeneously suspended in the liquid phase. (6) effectively delivers nutrients to the algae. The active flow (7) simultaneously promotes uniform and rapid growth of the algae in the container 12. In other words, discovery of the active flow (8) advantageously, enables algae production in a deep vessel container. (9) The active flow also effectively moves the algae through the container to the outlet and to harvest.

The active flow (10) further advantageously reduces algal adhesion on the light source and/or on the light assembly and/or on the liftwall. Algae are known to adhere onto the inner surfaces of a bioreactor. Algae adherence to the light sources diminishes light emittance. A reduction in light emittance is deleterious as it reduces the growth of the algae. The unique active flow with its helical flow component and its turbulent flow component reduces, or prevents, algae adhesion to the light assembly/the individual light sources by maintaining a steady multi-directional flow pattern in the container 12. In this way, the active flow promotes algae growth by reducing algae adhesion on the light sources.

The present active flow is distinct from laminar flow. "Laminar flow" is fluid flow in parallel layers, with no disruption between the layers. The present active flow, on the other hand, has a helical flow component (flowpath 20+lift G)

and a turbulent (or micro-turbulent) flow component (diffuser 28). Thus, the present active flow includes non-laminar flow components.

The present active flow is distinct from turbulent flow. "Turbulent flow" is a fluid regime characterized by chaotic or random property changes. The present active flow is includes a turbulent (or micro-turbulent) flow component but includes additional flow components for an overall flow profile that is distinct from turbulent flow. In contrast to turbulent flow, the active flow is not chaotic or random. Rather, the active flow is controllable. Control of the water flow into the inlet 14 controls flow velocity and magnitude along the flowpath 20. Control of the volume and/or pressure through the jets 50 controls the flow velocity and magnitude of the lift G. Control of the bubbles emitted by the diffuser 28 controls the turbulent flow component. Manipulation and/or control of the foregoing flow sources unexpectedly results in a manageable and measurable active flow. In other words, the foregoing flow sources can be controlled to produce an active flow with a quantifiable and measurable overall flow profile for the reliable growth of algae. The active flow can be controlled, manipulated and/or regulated.

The unique active flow produced by the present algae bioreactor has unexpected advantages particularly for the cultivation of algae. First, the active flow produces a thorough mixing of the algae suspension. A thorough mixing ensures uniform light exposure to each algae cell in algae suspension. Second, the active flow prevents adhesion of the algae on the light assembly. Unobstructed lighting increases algae growth, increases production efficiency, and reduces maintenance effort and cost. Third, control of flow parameters magnitude, volume, and flow rate can be used to prepare accurate growth models for the creation and calculation of reliable retention times, algae growth profiles, and harvest profiles. Thus, the active flow enables the accurate calculation of algae production models. The active flow enables the present algae bioreactor to overcome the structural and physical limitations confronted by conventional tubular algae bioreactors, for example. The active flow delivers the algae cells to the light and provides sufficient illumination to the entire algae suspension to maintain linear and/or exponential algae growth. Further advantages of the present active flow includes (i) moving and mixing the algae without imposing shear stress on the algae cells, (ii) prevention of algae cell sedimentation, (iii) improved $CO_2$ absorption, and (iv) prevention of $O_2$ build-up within the algae bioreactor 10.

In an embodiment, the algae bioreactor 10 includes one or more light zones and one or more dark zones. A "light zone" is an area within the container whereby the light sources emit light sufficient to generate photosynthesis conditions in the algae suspension. A "dark zone" is an area in the container whereby no light sources are present or light sources are not emitting light and/or are not emitting light sufficient for photosynthesis. It is understood that the algae bioreactor may include more than one light zone and more than one dark zone.

In an embodiment, the active flow moves the algae through the light zone I to photosaturate the algae cells as seen in FIGS. 3 and 3A. The algae then actively flow into the dark zone J where the photosaturated algae use up all the absorbed light energy for photosynthesis before they are exposed to light again in light zone K. In this way, the active flow and the spatial configuration of the light assemblies 22 in the container maximize the overall light utilization and maximize energy efficiency.

6. Thermal Gradient

In an embodiment, a thermal gradient is present in the algae suspension 18. A "thermal gradient," as used herein, is a temperature differential through a fluid body (in the present case, the fluid body is the algae suspension). In other words, a portion of the algae suspension (portion C) has a first temperature. Another portion of the algae suspension (portion D) has a second temperature less than the first temperature. The temperature differential between the portion C and portion D is from about 1° C. to about 50° C., or from about 5° C. to about 40° C. (or any value or subrange therebetween).

In an embodiment, the thermal gradient is formed or otherwise created by heating the portion C to a temperature greater than portion D. Portion C is heated by the provision of one or more thermal elements 30 in portion C (FIGS. 3, 3A, 8, and 9). The thermal element 30 can be a cooling element or a heating element. In an embodiment, the thermal element 30 is a heating element which heats portion C to a temperature from about 5° C. to about 15° C. greater than the temperature of portion D.

The thermal gradient creates convective movement within the algae suspension 18. The term "convection," (or "convective movement" or convectively moving") as used herein, is fluid motion caused by the transfer of heat from one location to another location. Bounded by no particular theory, it is believed that the density of the heated (warmer) algae suspension (portion C) is less than the density for the unheated (cooler) algae suspension (portion D) along the thermal gradient. The less dense heated algae suspension rises (portion C) and the more dense unheated algae suspension (portion D) sinks. This density differential caused by heat transfer within the algae suspension causes a rising and sinking motion producing fluid movement of the algae suspension 18. In particular, the algae suspension 18 convectively flows about and/or around the liftwall 24 at flow points E and F as shown in FIG. 8. As can be seen from FIG. 8, the thermal gradient TG extends vertically, or substantially vertically, through the algae suspension 18.

In an embodiment, the liftwall 24 is located at, placed on, along, adjacent to, directly adjacent to, a thermal gradient TG as shown in FIG. 8. The liftwall 24 may extend along some, or the entire extent, of the length and/or height of the thermal gradient TG. In this way, the liftwall 24 creates or otherwise defines the thermal gradient TG as shown in FIG. 8. The liftwall 24 operates as a boundary or a barrier between heated portion C of the algae suspension 18 and the unheated portion D of the algae suspension, containing heat from the thermal element 30. In this way, the liftwall 24 delineates between the heated portion C and the unheated portion D within the algae suspension to create the thermal gradient TG. Applicants have surprisingly discovered that placement of the liftwall 24 along the thermal gradient contributes to the helical flow of the algae around the liftwall 24. In other words, convection flow assists in the propulsion of the algae around the liftwall as indicated by the arrows through flowpoints E and F (FIG. 8).

7. Growth Profile

Algae have five phases of growth: (1) lag; (2) exponential; (3) declining growth rate; (4) stationary; and (5) death. The growth rate of the algae is a measure of the increase in biomass over time and it is determined from the exponential phase. The duration of the exponential phase in the algae bioreactor depends upon the size of the algae, the growth rate, the doubling time, the volume of the of the container, and culturing conditions to support algal growth. Nonlimiting procedures for biomass determination include cell count, dry weight, in vivo fluorescence, and turbidity.

The "retention time" is the amount of time a volume of the algae suspension remains in the container 12 until the volume of algae suspension is harvested. The retention time is based on the foregoing factors influencing the growth rate of the algae. In an embodiment, the algae bioreactor is configured to maintain the algae in a continuous exponential growth phase. New or recycled algae are introduced at the inlet portion A of the container. Algae growth continues as the algae (and/or the algae suspension) actively flow through the container 12 from the inlet end toward the outlet end. The active flow and light emittance from the light assemblies are adjusted so that at the outlet end of the container, the algae suspension is in an exponential growth phase. In an embodiment, control subsystems and sensors determine the optimal time for harvest. The active flow parameters, the lighting conditions, water quality, pH, $O_2$, temperature, and $CO_2$ are monitored and controlled to ensure continuous growth in the exponential phase.

In an embodiment, the retention time for the present algae bioreactor is from about 12 hours or about 1 day to about 4 days, or about 20 days, or about 24 days.

The algae bioreactor may optionally include one or more of the following subsystems: control, sensor, nutrient, filtration systems, electrical and/or instrumentation. Nonlimiting examples of components for these algae bioreactor subsystems include oxygen sensor, $CO_2$ sensor, pH sensor, light sensor, conductivity sensor, and/or recirculation pump. These subsystems may be operated alone or in concert to (1) maintain the algae in an exponential growth phase at harvest, (2) a continuous algae production cycle, and (3) a combination of (1) and (2).

8. Harvest

The algae bioreactor 10 and the components thereof may be configured to maximize algae harvest. Upon completion of the algae growth cycle, the algae are collected. The "harvest density" is the density of the algae in the algae suspension when the algae are removed from the container. In other words, the harvest density is the size/mass of the individual algae cells and the algae density of the algae suspension at the time of removal from the container. In an embodiment, the harvest density is from about 0.005 g/L, or about 0.01 g/L, or about 0.1 g/L, or about 1.0 g/L, or 1.5 g/L, or about 3.0 g/L, to about 7 g/L, or about 10 g/L, or about 20 g/L.

Harvest may occur (1) directly from the container 12 or (2) by way of transfer from the container 12 to a harvest tank. In an embodiment, harvest occurs by removing the (1) the active flow from the container 12 and (2) optionally removing the light assembly 22, and (3) optionally removing one or more of the following from the container: the liftwall 24, the gas conduit 26, the diffuser 28, and thermal element 30. The sources of the active flow (flow along the flowpath, gas conduit, and diffuser) are turned off, removing the active flow, and allowing sedimentation of the algae on the bottom wall 40. The settled algae is removed from the bottom of the container by way of a drain (not shown) located in the bottom wall 40. Once removed from the container, the algae is dewatered and further processed.

In an embodiment, the algae bioreactor is a component of a continuous algae production system. The outlet 16 is in fluid communication with a harvest tank 100 by way of a weir. The weir and the harvest tank 100 are configured to permit algae of greater than or equal to a predetermined threshold size to flow and pass over the weir and into the harvest tank 100. Algae cells less than the threshold size are re-circulated in the container 12 for continued growth. Alternatively, the algae suspension may be moved via a conduit, pipe, or channel to a harvest tank. The active flow continues in the container 12.

The active flow is not present in the harvest tank 100, permitting sedimentation in the harvest tank 100. The algae settle in the harvest tank 100 where the algae is dewatered. Dewatering may be performed by way of separation, centrifugation, flocculation, filtration, decantation, and any combination thereof.

In an embodiment, the water removed by the dewatering procedure is re-circulated back to the inlet portion A for re-use as shown by arrow L in FIG. 3. The re-circulated water can include algae. The re-circulated water can be pre-treated as desired. The algae bioreactor 10 advantageously enables the continuous production and harvest of algae.

The scalable nature of the algae bioreactor 10 enables algae production yields from about 1 g/day, or 10 g/day, or 100 g/day, or 1 kg/day to 10 kg/day, or 100 kg/day, or 1000 kg/day, to 10,000 kg/day, or 100,000 kg/day, or 1,000,000 kg/day or more.

Harvest of the algae may include one or more of the following procedures: flocculation (cellulose), settling, dewatering, filtration, and any combination of the foregoing.

The dewatered algae are then subjected to an extraction procedure which separates the algae into an oil component and a solids or pulp component. Nonlimiting examples of suitable extraction procedures include expeller/press, solvent (hydrocarbon, hexane, benzene) extraction, and/or supercritical fluid extraction (pressure/heat cell rupture).

The algal oil retrieved can be processed into a fuel, such as a biodiesel. This may or may not include a transesterification procedure. Thus, the present bioreactor advantageously produces a renewable energy from the algae—a viable alternative fuel source to petroleum-based fuels.

Nonlimiting examples of applications for the harvested algae (i.e., algal oil and/or the algal biomass) include fuel, food, pharmaceuticals, cosmetics, nutritional supplement, fertilizer, pollution control, pigments, and/or food stabilizer.

The present algae bioreactor may comprise two or more embodiments disclosed herein.

9. System

The present algae bioreactor may be a component of a system as shown in FIG. 1. Nonlimiting examples for the source of the water 2 (FIG. 1) for the algae suspension include effluent from an anaerobic digester, effluent from a (municipal) waste water treatment facility, waste water from a power plant, and/or waste water from a manufacturing plant.

In an embodiment, the effluent from an anaerobic digester is the water source for the present algae bioreactor. The anaerobic digester may be located next to the algae bioreactor. The anaerobic digester and the algae bioreactor may share one or more common walls which promotes construction, and/or thermal efficiencies as well as other production efficiencies.

The gas 6 (FIG. 1) introduced into the present algae bioreactor may originate from a variety of sources. For example, the gas may be an exhaust gas as discussed above. Nonlimiting sources for the exhaust gas (or flue gas) include coal or other fossil-fuel fired power plants, vehicles (cars, trucks), manufacturing facilities (i.e. a steel production plant), and other hydrocarbon powered (i.e., methane) combustion engines. The bubbling of an exhaust gas (from a power plant, for example) into the present algae bioreactor provides a system for removing $CO_2$ from the atmosphere. The exhaust gas may be captured from any of the foregoing sources and either (i) introduced directly into the present algae bioreactor or (ii) stored (i.e., in tanks) for subsequent introduction into the algae bioreactor.

Conventional algae production systems (farms, tubes, bags) attempt to maximize the surface area of algae sunlight exposure. Many of these systems require a geographical location with relatively high annual sunlight, temperate climate, and vast areas of land to accommodate large, shallow ponds (or vast stretches of tubes) of algae. The premise of surface area maximization inherently entails inefficiencies. A fundamental inefficiency is water evaporation and/or the energy and transportation costs of water supply.

The present deep-vessel algae production system is a novel and unique approach to algae production. By "bringing the light to the algae with active flow" the present deep-vessel algae production system operates on a fundamentally different premise than surface-area-based systems. Accordingly, the present deep-vessel system avoids many of the inherent problems of these systems. The present deep-vessel algae production system has no geographic restriction. Thus, the present deep-vessel system can be built almost anywhere such as near a water source (i.e., near any ocean, sea, inland lake or the Great Lakes, for example).

By tailoring the light source to the wavelength for optimal algae photosynthesis, the energy cost for the light component of the present system is surprisingly low. In addition, the active flow ensures an energy-efficient (i) algal light exposure, (ii) a controllable growth profile, and (iii) a controllable harvest. In this way, the present deep-vessel system with active flow surprisingly exhibits versatility and scalability with low production energy requirements that are unmatched by conventional algae production systems.

The present system may comprise two or more embodiments disclosed herein.

The present disclosure provides a process. In an embodiment, a process for producing algae is provided and includes introducing an algae suspension into a container comprising an inlet, an outlet, a light assembly, a liftwall, a gas conduit, and optionally a diffuser. The container can be any container with components as disclosed above. The container is configured to provide photosynthesis conditions to the algae suspension as disclosed above. The process includes moving the algae around the liftwall in a helical manner. The flowpath and the lift G create the helical flow motion of the algae.

In an embodiment, the liftwall includes a light source as previously disclosed. The process includes emitting light from the liftwall onto the algae as the algae helically travel around the liftwall.

In an embodiment, the process includes actively flowing the algae suspension from the container inlet to the container outlet. In other words, the active flow provided by the container, moves algae from the container inlet to the container outlet.

In an embodiment, the active flow of the process includes helically moving the algae around the liftwall. The active flow includes the helical flow component (flowpath+lift G) which moves the algae in a serpentine manner about or around the liftwall as disclosed above.

In an embodiment, the active flow of the process includes turbulently flowing (or micro-turbulently flowing) the algae through the light assembly. The active flow includes the turbulent (micro-turbulent) flow component (diffuser) which mixes and moves the algae through the light assembly as disclosed above.

In an embodiment, the process includes growing the algae to a harvest density.

In an embodiment, the process includes harvesting the algae at the harvest density from the outlet.

In an embodiment, the process includes producing a biofuel from the algae harvested from the present algae bioreactor.

In an embodiment, the process includes preventing, or reducing, with the active flow adhesion of algae on the light assembly and/or on light sources.

In an embodiment, the process includes growing or otherwise culturing the algae in the exponential growth phase. Once a steady-state of exponential algae growth is achieved or otherwise maintained in the container, the process includes continuously harvesting the algae during the exponential growth phase. Harvest during the algae exponential growth phase advantageously enables continuous production of algae.

In an embodiment, the process includes actively flowing the algae suspension through a deep-vessel container. In other words, the algae suspension moves through a deep-vessel container by way of the active flow.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a physical or other property, such as, for example, length, or mass, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g. 1 to 5), one unit is typically considered to be 0.1. These are only examples of what is specifically intended, and all possible combinations of numerical values between the lowest value and the highest value enumerated, are to be considered to be expressly stated in this disclosure.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. An algae bioreactor comprising:
   a container comprising a bottom wall, an inlet, an outlet, and an algae suspension in the container;
   a flowpath moving from the inlet to the outlet;
   a light assembly;
   a liftwall forming a first flowpoint between the top of the liftwall and the suspension surface and a second flowpoint between the bottom of the liftwall and the bottom wall;
   a gas conduit extending along a length of the container interior, the gas conduit emitting gas bubbles into the algae suspension; and
   the flowpath and the emitted gas bubbles moving the algae in a helical motion around the liftwall.

2. The bioreactor of claim 1 wherein the liftwall is substantially parallel to the flowpath.

3. The bioreactor of claim 1 wherein the liftwall defines a first portion and a second portion in the container, the conduit located in the first portion and producing an upward fluid lift in the first portion.

4. The bioreactor of claim 3 comprising a diffuser located below the light assembly; and
   the flowpath, the emitted gas bubbles and the diffuser produce an active flow of the algae from the inlet to the outlet.

5. The bioreactor of claim 1 wherein the container holds the algae suspension under photosynthesis conditions.

6. The bioreactor of claim 1 wherein the liftwall comprises a light source.

7. The bioreactor of claim 1 wherein the container is a deep-vessel container.

8. The bioreactor of claim 1 comprising a light zone and a dark zone.

9. An algae bioreactor comprising:
- a container comprising a bottom wall, an inlet, an outlet and an algae suspension;
- a flowpath moving from the inlet to the outlet;
- a light assembly;
- a liftwall forming a first flowpoint between the top of the liftwall and the suspension surface and a second flowpoint between the bottom of the liftwall and the bottom wall;
- a gas conduit extending along a length of the container interior, the gas conduit emitting gas bubbles into the algae suspension;
- a diffuser located on a bottom wall of the container; and
- the flowpath, the liftwall, the gas conduit, and the diffuser producing an active flow of the algae from the container inlet to the container outlet.

10. The bioreactor of claim 9 wherein the liftwall comprises a light source.

11. The bioreactor of claim 9 comprising a thermal element for heating at least a portion of the algae suspension; and
the liftwall defines a thermal gradient in the algae suspension.

12. The bioreactor of claim 9 wherein the outlet is in fluid communication with a harvest tank.

13. The bioreactor of claim 9 wherein the bioreactor produces from about 1 kg algae/day to about 10,000 kg algae/day.

14. A process for producing algae comprising:
introducing an algae suspension into a container comprising a bottom wall, an inlet, an outlet, a light assembly, a liftwall, a gas conduit, and a diffuser wherein the liftwall forms a first flowpoint between the top of the liftwall and the suspension surface and a second flowpoint between the bottom of the liftwall and the bottom wall; and
actively flowing the algae suspension from the container inlet to the container outlet under photosynthesis conditions.

15. The process of claim 14 wherein the actively flowing comprises helically moving the algae around the liftwall.

16. The process of claim 14 comprising growing the algae to a harvest density.

17. The process of claim 16 comprising harvesting the algae at the harvest density from the outlet.

18. The process of claim 17 comprising producing a biofuel from the harvested algae.

19. The process of claim 14 comprising growing the algae in an exponential growth phase; and
continuously harvesting the algae during the exponential growth phase.

20. The process of claim 14 comprising actively flowing the algae suspension through a deep-vessel container.

* * * * *